US011352633B2

(12) United States Patent
Chen et al.

(10) Patent No.: US 11,352,633 B2
(45) Date of Patent: Jun. 7, 2022

(54) AUREOBASIDIUM PULLULANS STRAINS WITH HIGH-YIELD HEAVY OIL AND CONSTRUCTION METHOD AND APPLICATION THEREOF

(71) Applicant: Tianjin University of Science and Technology, Tianjin (CN)

(72) Inventors: Yefu Chen, Tianjin (CN); Siyao Huang, Tianjin (CN); Peng Zheng, Tianjin (CN); Yuanhua Wang, Tianjin (CN); Jian Guo, Tianjin (CN); Mengjuan Zhang, Tianjin (CN); Xuewu Guo, Tianjin (CN); Dongguang Xiao, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 0 days.

(21) Appl. No.: 17/070,948

(22) Filed: Oct. 15, 2020

(65) Prior Publication Data

US 2021/0024942 A1 Jan. 28, 2021

(30) Foreign Application Priority Data

Oct. 15, 2019 (CN) ........................ 201910978113 .1

(51) Int. Cl.

| | |
|---|---|
| ***C12N 15/80*** | (2006.01) |
| ***C12N 9/88*** | (2006.01) |
| ***C12N 15/90*** | (2006.01) |
| ***C12P 7/6463*** | (2022.01) |

(52) U.S. Cl.
CPC ............... *C12N 15/80* (2013.01); *C12N 9/88* (2013.01); *C12N 15/902* (2013.01); *C12P 7/6463* (2013.01)

(58) Field of Classification Search
CPC .............................. C12N 15/80; C12N 15/902
See application file for complete search history.

(56) References Cited

U.S. PATENT DOCUMENTS

2017/0016039 A1 1/2017 Skory et al.

FOREIGN PATENT DOCUMENTS

| | | |
|---|---|---|
| CN | 109136109 A | 1/2019 |
| CN | 110066802 A | 7/2019 |

OTHER PUBLICATIONS

Jian Guo et al., Development of a one-step gene knock-out and knock-in method for metabolic engineering of Aureobasidium pullulans, Journal of Biotechnology, 2017, pp. 145-150, vol. 251.
Byung-Kwan Kang, et al., Production of pure beta-glucan by Aureobasidium pullulans after pullulan synthetase gene disruption, Biotechnol Lett, 2010, pp. 137-142, vol. 32.
David Machaku, et al., Fermentative production of liamocin by Aureobasidium pullulans, Journal of Zhejiang University of Science and Technology, 2017, pp. 414-418, vol. 29 No. 6.
Rui-Rui Tang, et al., Overexpression of a pyruvate carboxylase gene enhances extracellular liamocin and intracellular lipid biosynthesis by Aureobasidium melanogenum M39, Process Biochemistry, 2018, pp. 64-74, 69.
Katharina Maria Saur, et al., A pH shift induces high-titer liamocin production in Aureobasidium pullulans, Applied Microbiology and Biotechnology, 2019.

*Primary Examiner* — Antonio Galisteo Gonzalez
(74) *Attorney, Agent, or Firm* — Bayramoglu Law Offices LLC

(57) ABSTRACT

An *Aureobasidium pullulans* recombinant strain with high-yield heavy oil and a construction method and application thereof are provided. The *Aureobasidium pullulans* recombinant strain is obtained by knocking out a pullulan synthetase PUL gene while overexpressing an ACL gene. The obtained *Aureobasidium pullulans* recombinant strain can significantly increase the yield of heavy oil. After 7-day fermentation with xylose as carbon source, the yield of the heavy oil of the recombinant strain reaches 19.4372 g/L, while the yield of the heavy oil of the original strain is 10.0325 g/L, i.e. the recombinant strain improves the yield by 93.74% compared with the original strain.

6 Claims, 6 Drawing Sheets

Specification includes a Sequence Listing.

SEQUENCE LISTING

```
<160> NUMBER OF SEQ ID NOS: 28

<210> SEQ ID NO 1
<211> LENGTH: 1462
<212> TYPE: DNA
<213> ORGANISM: Aureobasidium pullulans P30

<400> SEQUENCE: 1

atgtccgcaa agtcgatcct cgaagccgat ggcaaggcca tcctcaacta ccaccttacc      60

agagctcctg tcatcaagcc cactcctctt cccccagctg ccaaccacaa ccctcacgcc     120

aagctctgct ccctctactt ccctgagggt gcttccgcca aggacatcct tgatgaggct     180

gaggtcaagt acccctggtt gcacgagtct ggcgccagat ttgttgcaaa gcccgatcag     240

ctcatcaagc gacgaggcaa gagcggcctt ttggccttga acaagacctg ggctgaggcc     300

agagcatggg ttgaggagcg tgccggcaag aaccagagag tcgagactgt tgatggtgtc     360

ctgagacagt tcttggtcga gcctttcgtg cctcaccccc aagacaccga gtactacatc     420

aacatcaact ccgtccgtga gggtgactgg atcctcttca ctcacgaggg tggtgtcgat     480

gtcggtgatg tcgatgctaa ggctgagaag cttttgatcc ccgtcgacct caaggagtac     540

ccttcaaacg aggagattgc tgccactctc ctcaagaagg tccctcaggg tgtccacaac     600

gtcctcgttg acttcatctc ccgcctctac gccgtctacg ttgactgcca gttcacctac     660

ctcgagatca accctctcgt tgtcatcccc aacgctgatg ccacctctgc tgaggttcac     720

ttccttgact tggctgccaa gctcgaccag actgctgagt tcgagtgtgg tgccaagtgg     780

gccatcgctc gctctgctac tgctctcggc ttgaacgtcg ctgacaagaa ggacaccaag     840

gtctccatcg atgtcggtcc tcctatggag ttccctgctc ccttcggtcg tgaaatgtcc     900

aaggaggagg cttacattgc cgagatggat gctaagactg gtgcttccct caagctgacc     960

atcctcaacg gcaacggtcg tgtctggacc cttgtcgctg gtggtggtgc ttcggtcgtc    1020

tacgccgatg ccatcgcctc tgctggttac gctagtgagc ttgccaacta cggcgagtac    1080

tctggtgctc ccaccgagac tcagaccttc cactacgcca gaaccgtcct tgacctcatg    1140

ctccgtgccc ccatgcaccc cgagggcaag gtcctcttca ttggtggtgg tattgccaac    1200

ttcaccaacg ttgcctctac tttcaagggt gtcattcgcg ccctccgtga ggttgctcct    1260

ctcctcatcg agcacaacgt caagatctgg gtccgccgtg ctggtcccaa ctaccaggag    1320

ggtctcaaga acatcaaggc cgtcggtcaa gagctcaagc tcgacatgca cgtcttcggt    1380

cctgagatgc acgtctctgg tatcgtcccc cttgccctcg tccccggcaa gtacactccc    1440

gacatcaagg agttcggtgc at                                             1462


<210> SEQ ID NO 2
<211> LENGTH: 991
<212> TYPE: DNA
<213> ORGANISM: Aureobasidium pullulans P30

<400> SEQUENCE: 2

tgcgactatg ttatgatcgc gaccaggcag tcatagctat catgtggtgt ttatgctaga      60

gaaggctgtg tagctgtacg accctcggca tctattttga gatgctggtc gtgatgtgca     120
```

-continued

```
atgcgggatg atgcagtgca gcacagaaca cacaccaggc acacgttttt tgctaggcgt    180

ttcagagcaa ctgacaaaag tgctcgcgac acattcgtca tgttgatcat ggttgggaag    240

gcatgctggg taggtgcatg aatataacaa caggtctttc ttgccaatcc tccttctctc    300

ttcactcttc cctaaacaca cctttccatt acagccaaat cctttttcag acatcaagaa    360

cagaacgttc tcagcagtaa ccttgaatat ctactacaac atgcgcttct ccatcttcgc    420

tctcgccgcc tctctggccg ctgtggtgac tgctacccct atcgtcaaac gcgcatccat    480

taacagcacg caaccattct atctcctaac aaccgactca ccaacctact ctcaaaacac    540

ttctcgcctc ccaaacgtct ctttgactac cctcttcgat ccctactacc aacccaacaa    600

cctgctccgc ctcatcggtc ccggctacgg cagagtcccc caattcacac tttccgatgg    660

agtattgcac acacccggca agggaccaca cggtatcggc gactacatct acaacagcac    720

tgaagtccac accggctcgg agttgcaatt cagagccgaa tacgaaggag ctggagattt    780

gaccctcgag aagggatatc tgcttggtgt gaatggaagc acaactggat ggatcatctg    840

cgtggaggag ttgggtcaga gtgttgtaag tttgcttgtg ttaaagattt ctggggagat    900

atgtactgac gatgaacaga ttgagtggaa gggcacagat gagggatgca cgcggaccta    960

catccaggct gctttgactg tgccttacta a                                   991


<210> SEQ ID NO 3
<211> LENGTH: 1500
<212> TYPE: DNA
<213> ORGANISM: Aureobasidium pullulans P30

<400> SEQUENCE: 3

ggtagcctgg cccttgacac cttcaatgac atcgtcgagg gtcaagacag caagaacggg     60

aacaccagtc tcctggcgaa cctggccgat ggtgctgggt ctgtcggagc cgtcatcagg    120

cttgccctcc ttctcgctct gactgggagt cttctcctgt ctgtcgaggg caacgataat    180

gccaacgagc tcaccaccct ggctcttgat aatgctgatg gcctctctga tggcagtgcc    240

ggcagtcatg acatcgtcaa tgacaacaac cttcttgccc ttgaggctct cgccaaccat    300

cagaccaccc tcgccatggt ccttgacctc cttgcggttg taaacgaagc cgaggtcgcc    360

atactttgcc tcgtcaatgc cagcaagctt ctcggcagtg gtggcgcaaa gaggaatacc    420

cttgtaggca gggccgaaga ggacgtcaaa cttgaactct gggtgggcgg agcaatactc    480

ggcgatagta cgagcgtagg cctcgctgat gccgcggatg agcttgccct tggagaacag    540

accacagttg aagaagtaag gcgagatacg gccggacttg agggtgaagg agccaaaggt    600

caagatgttg gacgagaggg tgagcgagat gaggtcgcgc ttgtaggcgg ggagagcttc    660

tgcggaagac attggtggcg gcggggtagc aaaagtggat agcaaaggaa tagtaaaagg    720

agggttcaga tacaaattag caacaggcca ggctagacgc gcgactatcc actgcggcaa    780

atggtgagct gcaagcaacg gtaagatgtg acaggacgac gagcggtgtg ccggaaaaaa    840

attggagggg cagcgcacag cggcggctgt tcctcagtgg tgcccaaacg ttatcgatag    900

taactacacc aagcatacgc agtgagcggc tatacagagg gaataatagg catatcggca    960

cgaatagaga gccctgagag cagttcattg agcatattgt cacgtggaat gcgatagctg   1020

tgtccaggtc gagacaccgc aagtgaaaga tacacacata gattctcgat tcaagcagtt   1080

tgcctccgcc accgcagtgc atagcaagca aaaaaaaacg acagttggct catcatccgt   1140

tacatcattt tttccagctg gctccgctct cagttggtgg gctcccaacg aagcagcaaa   1200

aaaagtgaga gaaaaaaact agcttggcgg ggcaactgaa gctagaccct ttggctcgct   1260
```

```
tagtcagtgc gctggctcac acacactcaa aaaggccacc cctcccgcgc ccttcttctc   1320

atcaccgtct tcataccacg gttcgtcaag caatcgtatc tggtaagctt tgacctcttg   1380

agcgggctcc actttgctat ttcttggatc tgctcttctt tttcttcctt cctctttttc   1440

taacctctct tcagaaagtt caaccgtact tcactccatc ttccatacac aaccgtcaac   1500


<210> SEQ ID NO 4
<211> LENGTH: 500
<212> TYPE: DNA
<213> ORGANISM: Aureobasidium pullulans P30

<400> SEQUENCE: 4

acgatttgac acttttgtct ttcaaaagct tgtctcttct ttgcttcggt gttcttctca     60

aggtcacatg agttgagcat ttcactaacg ataccacctt tctgctgtca cgaccttgca    120

tgaaacatga tggcgaggca gttgcttcga gggatctggg tttacggctt agattattag    180

tctgcagcag caattcaaaa ctcattgttg attgcacacc atctcttttt gactttccat    240

ttgctttata tgtgctctgc tgtaccttcg ctactctccg tgacctctcg tctactttct    300

tgcgtgctct cgagtgtctc ttgtaatgct gctcggtcgc ttggactgtc acgactgtct    360

tgctgagccc attgtcgcaa gtcggtcaat catgatcact ctacgcctct atctcgcttg    420

gtatccttgc gcacttgctt cattcatgct ttgaaaagtg ctcgctgttg cgctgctgtc    480

cgacctagtg aaagggaaga                                                500


<210> SEQ ID NO 5
<211> LENGTH: 1454
<212> TYPE: DNA
<213> ORGANISM: Aureobasidium pullulans P30

<400> SEQUENCE: 5

cattgcctca cttaggtaac ctctcggcgc tgacctgctt gtttccgcga cagcctctcc     60

tacacacctt agtattcatc accgaattaa tcatggtctc ctttttggtg tccaagttca    120

acagctacta tgctgcgaga ccaggtatga ttgagacttg cgacatgtct tgtgactctg    180

tgctaacctt cgtttcagtg cttacgacca tggtcaccaa cgccgtaagt ccatttacga    240

ccacacgctg aaatgtgttc ctgacgtctc gtccaggtgc ttggtggtgt agccgacact    300

gtcgcccaaa ctctcacagc agtcagagaa cgtgccgttc gcaaacctgg tggccccgac    360

cccaagaacg atcgattggc cattgagatt catgagatag accgcagaat ctctgaggaa    420

gagctcatcc ctgattccaa ggtgctgcct ccaccgttcg actttgagag gtacaaggaa    480

ccaagagcaa gaaacaagga ttcaaaaatg ctgatacact gggcagattg acaagattca    540

tggcatatgg ttttattatg gctcccgtcc aacacaagtg gttcggcttc ctcaatcgca    600

ttttccctct tgccaaggga gctggcacca gcgcagcagc aaagagaacc gcctttgacc    660

agcttctgtt tgcaccggtt ggtctcggag ccttcttcac tttcatgact gtggcagaag    720

gaggcggccg taaggagatt cagaagaagt tccaggatat ctatattcct tctctcaagg    780

ccaactactt ggtctggcct gctgtacagc tgatcaactt cagacttatg ccgcgtcagt    840

tccagattgt aagtggtatc tgactttaac tgaagagcag cgactaacac tgttacagcc    900

atttgtgtcg accgttggta ttgcatggac ggcctacctt tctctgacca actcggcaga    960

ggaggcttag aaagccattc acaaggaaca aatcgggaca gtgtgttgat tacctaggta   1020

tcttcaagca tccatcggac agcgggatag gcaggcgttc tggcgacttt acggggcgtt   1080
```

-continued acgggccgat agacacgtcg cttggtgcaa ggcatcttga atgatacagt gattgagatg 1140
tgcaacttca agcaggatat atggtgcgac atcgagtgaa gcaggtgatc taatggggct 1200
ctgtatatag ataggtcatg attggtgata tcagttgata gacaacacga gagagggcac 1260
gaatgctcgg aagcacatcg gtcgtgacgc atttttcgag ctgcccctcg tcccgaccgc 1320
cggaagctgt tggggaaaga ctcaagcccc tcacacacca caacaaccca tcaagcactg 1380
ttgtatataa ctgtacgtct ttgtctgctg ctgtctctca caccaaactg tctgacacac 1440
tcgattcagt caca 1454

<210> SEQ ID NO 6
<211> LENGTH: 620
<212> TYPE: DNA
<213> ORGANISM: Aureobasidium pullulans P30

<400> SEQUENCE: 6
atctctgatg tgcgtatgac caagctctaa atctgcaaag aggaagagca aatattatga 60
aaatgggttt cgagcgtcac tggcatacat gactgcaaga ggcttttctt tatctcacta 120
cttcatcatc gaagaaatga catgtgttta cgtccacgat cctgctctat ctcctgtgct 180
ccttttctgt gatgttgttg cttcctgtca aaccttggcc acagcatgat ttagtgatca 240
cattcggtat ccaaccgagc cacacatctc cgtgccaacg cgtctccata cttctgtctt 300
ctggaacgag caacaagccc ttgtgatgaa gccatcaacc accttgtttc atggcacaaa 360
cccgctctcg gggagacaaa tgtttgtact tgaaactcgc gttccttagc actcctcctg 420
acgacacttc tcacgctctt gttcagtttc atgctcgtgg tagaagcatg tgttatcccc 480
gaactgaggc atgtcatctg ccgtcagata aacacgatcc gcatcgacct ctgacaggcc 540
gtttctggta ctggctcgcg aatagcagcc acggcactgc tttggtggca gtcttctgcc 600
cagagaaacc atgaccttag 620

<210> SEQ ID NO 7
<211> LENGTH: 40
<212> TYPE: DNA
<213> ORGANISM: Artificial Sequence
<220> FEATURE:
<223> OTHER INFORMATION: The sequence is synthesized.

<400> SEQUENCE: 7
ctagaggatc cccgggtacc gtcaagacag caagaacggg 40

<210> SEQ ID NO 8
<211> LENGTH: 42
<212> TYPE: DNA
<213> ORGANISM: Artificial Sequence
<220> FEATURE:
<223> OTHER INFORMATION: The sequence is synthesized.

<400> SEQUENCE: 8
cggtgagttc aggctttttc atgttgacgg ttgtgtatgg aa 42

<210> SEQ ID NO 9
<211> LENGTH: 42
<212> TYPE: DNA
<213> ORGANISM: Artificial Sequence
<220> FEATURE:
<223> OTHER INFORMATION: The sequence is synthesized.

<400> SEQUENCE: 9
ttccatacac aaccgtcaac atgaaaaagc ctgaactcac cg 42

<210> SEQ ID NO 10
<211> LENGTH: 40
<212> TYPE: DNA
<213> ORGANISM: Artificial Sequence
<220> FEATURE:
<223> OTHER INFORMATION: The sequence is synthesized.

<400> SEQUENCE: 10
agacaaaagt gtcaaatcgt ctattccttt gccctcggac 40

<210> SEQ ID NO 11
<211> LENGTH: 39
<212> TYPE: DNA
<213> ORGANISM: Artificial Sequence
<220> FEATURE:
<223> OTHER INFORMATION: The sequence is synthesized.

<400> SEQUENCE: 11
gtccgagggc aaaggaatag acgatttgac acttttgtc 39

<210> SEQ ID NO 12
<211> LENGTH: 40
<212> TYPE: DNA
<213> ORGANISM: Artificial Sequence
<220> FEATURE:
<223> OTHER INFORMATION: The sequence is synthesized.

<400> SEQUENCE: 12
gtgaattcga gctcggtacc tcttcccttt cactaggtcg 40

<210> SEQ ID NO 13
<211> LENGTH: 22
<212> TYPE: DNA
<213> ORGANISM: Artificial Sequence
<220> FEATURE:
<223> OTHER INFORMATION: The sequence is synthesized.

<400> SEQUENCE: 13
tgattacgcc aagcttgcat gc 22

<210> SEQ ID NO 14
<211> LENGTH: 23
<212> TYPE: DNA
<213> ORGANISM: Artificial Sequence
<220> FEATURE:
<223> OTHER INFORMATION: The sequence is synthesized.

<400> SEQUENCE: 14
gtaaaacgac ggccagtgaa ttc 23

<210> SEQ ID NO 15
<211> LENGTH: 23
<212> TYPE: DNA
<213> ORGANISM: Artificial Sequence
<220> FEATURE:
<223> OTHER INFORMATION: The sequence is synthesized.

<400> SEQUENCE: 15
tcggcatcta ttttgagatg ctg 23

<210> SEQ ID NO 16
<211> LENGTH: 49
<212> TYPE: DNA
<213> ORGANISM: Artificial Sequence
<220> FEATURE:

-continued

<223> OTHER INFORMATION: The sequence is synthesized.

<400> SEQUENCE: 16
gtgttcccgt tcttgctgtc ttgacggttg ttaggagata gaatggttg 49

<210> SEQ ID NO 17
<211> LENGTH: 50
<212> TYPE: DNA
<213> ORGANISM: Artificial Sequence
<220> FEATURE:
<223> OTHER INFORMATION: The sequence is synthesized.

<400> SEQUENCE: 17
gcaaccattc tatctcctaa caaccgtcaa gacagcaaga acgggaacac 50

<210> SEQ ID NO 18
<211> LENGTH: 45
<212> TYPE: DNA
<213> ORGANISM: Artificial Sequence
<220> FEATURE:
<223> OTHER INFORMATION: The sequence is synthesized.

<400> SEQUENCE: 18
gagaggttac ctaagtgagg caatgtcttc cctttcacta ggtcg 45

<210> SEQ ID NO 19
<211> LENGTH: 46
<212> TYPE: DNA
<213> ORGANISM: Artificial Sequence
<220> FEATURE:
<223> OTHER INFORMATION: The sequence is synthesized.

<400> SEQUENCE: 19
ctgtccgacc tagtgaaagg gaagacattg cctcacttag gtaacc 46

<210> SEQ ID NO 20
<211> LENGTH: 42
<212> TYPE: DNA
<213> ORGANISM: Artificial Sequence
<220> FEATURE:
<223> OTHER INFORMATION: The sequence is synthesized.

<400> SEQUENCE: 20
gaggatcgac tttgcggaca ttgtgactga atcgagtgtg tc 42

<210> SEQ ID NO 21
<211> LENGTH: 46
<212> TYPE: DNA
<213> ORGANISM: Artificial Sequence
<220> FEATURE:
<223> OTHER INFORMATION: The sequence is synthesized.

<400> SEQUENCE: 21
gtctgacaca ctcgattcag tcacaatgtc cgcaaagtcg atcctc 46

<210> SEQ ID NO 22
<211> LENGTH: 47
<212> TYPE: DNA
<213> ORGANISM: Artificial Sequence
<220> FEATURE:
<223> OTHER INFORMATION: The sequence is synthesized.

<400> SEQUENCE: 22
gcttggtcat acgcacatca gagatatgca ccgaactcct tgatgtc 47

-continued

```
<210> SEQ ID NO 23
<211> LENGTH: 47
<212> TYPE: DNA
<213> ORGANISM: Artificial Sequence
<220> FEATURE:
<223> OTHER INFORMATION: The sequence is synthesized.

<400> SEQUENCE: 23

gacatcaagg agttcggtgc atatctctga tgtgcgtatg accaagc                47


<210> SEQ ID NO 24
<211> LENGTH: 45
<212> TYPE: DNA
<213> ORGANISM: Artificial Sequence
<220> FEATURE:
<223> OTHER INFORMATION: The sequence is synthesized.

<400> SEQUENCE: 24

gttggtagta gggatcgaag agggtctaag gtcatggttt ctctg                  45


<210> SEQ ID NO 25
<211> LENGTH: 47
<212> TYPE: DNA
<213> ORGANISM: Artificial Sequence
<220> FEATURE:
<223> OTHER INFORMATION: The sequence is synthesized.

<400> SEQUENCE: 25

ctgcccagag aaaccatgac cttagaccct cttcgatccc tactacc                47


<210> SEQ ID NO 26
<211> LENGTH: 20
<212> TYPE: DNA
<213> ORGANISM: Artificial Sequence
<220> FEATURE:
<223> OTHER INFORMATION: The sequence is synthesized.

<400> SEQUENCE: 26

tagtaaggca cagtcaaagc                                              20


<210> SEQ ID NO 27
<211> LENGTH: 24
<212> TYPE: DNA
<213> ORGANISM: Artificial Sequence
<220> FEATURE:
<223> OTHER INFORMATION: The sequence is synthesized.

<400> SEQUENCE: 27

agaaggctgt gtagctgtac gacc                                         24


<210> SEQ ID NO 28
<211> LENGTH: 23
<212> TYPE: DNA
<213> ORGANISM: Artificial Sequence
<220> FEATURE:
<223> OTHER INFORMATION: The sequence is synthesized.

<400> SEQUENCE: 28

ttagtaaggc acagtcaaag cag                                          23
```

AUREOBASIDIUM PULLULANS STRAINS WITH HIGH-YIELD HEAVY OIL AND CONSTRUCTION METHOD AND APPLICATION THEREOF

CROSS REFERENCE TO RELATED APPLICATION

The present application is based upon and claims priority to Chinese Application No. 201910978113.1, filed on Oct. 15, 2019, and entitled "*Aureobasidium pullulans* Strains with High-yield Heavy Oil and Construction Method and Application thereof", the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named "GBRSMJ003_sequence listing.txt", created on 10/14/2020 and is 13,997 bytes in size.

TECHNICAL FIELD

The present invention relates to the technical field of genetic engineering, specifically to the synthesis of liamocins (Liamocin oils) and particularly to the overexpression of an ATP-citrate lyase (ACL) gene to increase the yield of heavy oil of *Aureobasidium pullulans*, so that the content of heavy oil is significantly increased.

BACKGROUND

*Aureobasidium pullulans* is a polymorphic saprophytic fungus with a very complex life history that belongs to Deuteromycota, Moniliales and *Aureobasidium*, and during growth and development, has the forms of yeast-like cells, blastospores, swollen spores, chlamydospores and mycelial cells.

Heavy oil, which is a microbial oil and an important secondary metabolite of *Aureobasidium pullulans*, is higher in density than water and generally deposits at the bottom of a fermentation broth. The heavy oil is classified into two types, namely alkane and polyol ester (Liamocins), wherein the alkane-type heavy oil is generally long-chain n-alkane with more than twenty carbons, and the liamocins-type heavy oil is formed by combining a mannitol or xylitol as a head group with 3-5 3,5-dihydroxydecanoic acids as a tail. Because of their special structure, the liamocins have great application potential. In medical treatment, the liamocins achieve anti-proliferation effects on various human tumor cells during medical treatment such as lung cancer cells, leukemia cells, breast cancer cells and cervical cancer cells, which are all inhibited, and have no influence on normal cells; in the chemical industry, the liamocins can be applied as surfactant, biodiesel or the like; in agriculture, the liamocins can be applied as antibacterial agent and pesticide to achieve powerful inhibitory effects on the activity of gram-positive bacteria such as *streptococcus.*

At present, the yield of the heavy oil of the *Aureobasidium pullulans* is not high, research on the heavy oil still remains in a preliminary stage, studies in molecular level are few, the synthesis mechanism of the *Aureobasidium pullulans* is still not clear. Li et al. disclosed a hypothetical pathway for heavy oil biosynthesis, and with an *Aureobasidium pullulans* strain P5, achieved production of a mannitol-type heavy oil with a single non-acetylated 3,5-dihydroxydecanoate group. In such case, acetyl coenzyme A to malonyl coenzyme A is catalyzed by the 3-ketoacyl synthase subunit (KS) of type I polyketide synthase (PKS) into the C4 portion of a reduction cycle, catalyzed by 3-ketoacyl-ACP reductase (KR), dehydrated by a dehydratase (DH) and lastly reduced by enoyl reductase (ER). According to another pathway, the malonyl coenzyme A is condensed into the C6 portion of the reduction cycle, then subjected to secondary condensation by the KS and reduced by the KR to produce a single 3,5-dihydroxydecanoate ester group of the acyl carrier protein (ACP) that remains bound to the PKS. Such a process requires 3-hydroxydecanoyl-ACP encoded by a pha G gene: CoA transacylase (pha G) releases a 3,5-dihydroxydecanoate ester group in an ACP derivative, and then mannitol is added, wherein the mannitol is prepared from glucose, and mannitol phosphate dehydrogenase (MDP1) and mannitol dehydrogenase (MDH2) are key enzymes in the synthesis pathway of the mannitol. Since the hypothetical pathway of heavy oil biosynthesis remains unclear in certain aspects, a large number of experiments are still required to further study the synthesis mechanism.

Besides, some studies also show that the productivity of known heavy oil producing strains is limited by the variety of carbon sources, which makes a significant difference in heavy oil production. Certain scholars performed fermentation optimization on the *Aureobasidium pullulans*, leading to yield increase of the heavy oil when glucose served as the carbon source, but the content of polyol ester therein was not high. The yield of heavy oil obtained through fermentation with other carbon sources is very low, mostly around 4.0 g/L. Researchers have also attempted to increase the yield of heavy oil via genetic modification approaches, among which overexpression of the coding gene of pyruvate carboxylase was applied to increasing the yield of heavy oil.

SUMMARY

The present invention provides an *Aureobasidium pullulans* recombinant strain capable of improving the yield of heavy oil and a construction method thereof, which solves the problem of low heavy oil productivity of *Aureobasidium pullulans* when xylose is used as a carbon source for fermentation.

The technical solution used by the present invention is as follows:

An *Aureobasidium pullulans* recombinant strain for improving the yield of heavy oil, the recombinant strain is achieved by using an *Aureobasidium pullulans* strain as an original strain, using an ACL gene as a substitute for a pullulan synthetase (PUL) gene and overexpressing the ACL gene with a strong promoter.

The ACL gene is an endogenous gene, and the nucleotide sequence of the ACL gene is as shown in SEQ ID NO: 1 in a sequence table.

The nucleotide sequence of the PUL gene is as shown in SEQ ID NO: 2 in the sequence table.

In some embodiments, the strong promoter is a PGK promoter.

In some embodiments, the original strain of the *Aureobasidium pullulans* strain is specifically an *Aureobasidium pullulans* P30 strain with the preservation number of CGMCC No. 13988.

The present invention also provides a construction method of the *Aureobasidium pullulans* recombinant strain:

taking an *Aureobasidium pullulans* strain as the original strain and the PUL gene as an integration site, sequentially connecting and integrating an upstream homologous arm FA of the PUL gene, a hygromycin (hyg) resistance gene fragment, the PGK promoter, the ACL gene, a GAP terminator and a downstream homologous arm FB of the PUL gene into the integration site, and performing homologous recombination to obtain the recombinant strain.

Preferably, the specific steps of the construction method of the *Aureobasidium pullulans* recombinant strain are as follows:

(1) carrying out PCR (polymerase chain reaction) amplification with the genome of the *Aureobasidium pullulans* strain as a template to obtain the upstream and downstream homologous arms FA and FB of the PUL gene, the PGK promoter, the GAP terminator and the ACL gene;

(2) carrying out PCR amplification on a plasmid carrying a hyg resistance gene to obtain the hyg resistance gene fragment; and (3) performing electrotransformation to sequentially connect and integrate the above-described PCR amplification products of the upstream homologous arm FA, the hyg resistance gene fragment, the PGK promoter, the ACL gene, the GAP terminator and the downstream homologous arm FB into the integration site, and performing homologous recombination to obtain the recombinant strain overexpressing the ACL gene with the strong PGK promoter.

In some embodiments, in step (2), the steps for constructing the recombinant plasmid carrying the hyg resistance gene are as follows:

(a) carrying out PCR amplification with the genome of the *Aureobasidium pullulans* P30 strain as a template to obtain a TEF promoter fragment and a TEF terminator fragment;

(b) carrying out PCR amplification with a Yep-HPT plasma as a template to obtain a hyg resistance gene fragment; and (c) fusing the TEF promoter fragment, the hyg resistance gene fragment and the TEF terminator fragment through fusion PCR to obtain a fused TEFp-hyg-TEFt fragment, and connecting the fused TEFp-hyg-TEFt fragment to a pUC19 plasma to obtain the pUC-HPT plasma.

Preferably, in the step (2), the hyg resistance gene fragment obtained through PCR amplification with the pUC-HPT plasma as the template is the TEFp-hyg-TEFt fragment.

The present invention also provides an application of the *Aureobasidium pullulans* recombinant strain to fermentation production of heavy oil.

Preferably, the method of fermentation production of heavy oil with the *Aureobasidium pullulans* recombinant strain is specifically as follows:

selecting and inoculating a strain seed into a seed culture medium, and performing shake culture at 28-30° C. and 200-240 r/min for 20-24 h to obtain a seed solution; inoculating the seeding solution at an inoculum size of 6%-8% into a fermentation culture medium, and performing shake flask fermentation at 28-30° C. and 200-240 r/min for 5-7 days;

wherein the seed culture medium is composed of 20 g/L of xylose, 1.0 g/L of yeast extract powder 4.0 g/L of $K_2HPO_4$, 0.8 g/L of $(NH_4)_2SO_4$, 0.2 g/L of $MgSO_4$, 4.0 g/L of NaCl and water as balance; the pH is 5.5-6.5, and sterilization is performed at 121° C. for 20 min; and the fermentation culture medium is composed of 50 g/L of xylose, 1.4-2.0 g/L of yeast extract powder, 0.8 g/L of $KNO_3$, 2.0 g/L of NaCl, 5.0 g/L of $K_2HPO_4$, 0.3 g/L of $MgSO_4$ and water as balance; the pH is 4.5-5.5 and sterilization is performed at 121° C. for 20 min.

The Yep-HPT plasmid and the hyg resistance gene described above are from the chapter of materials and methods of the article "Guo J, Wang Y, Li B, equivalent. Development of a one-step gene knock-out and knock-in method for engineering of *Aureobasidium pullulans* [J]. Journal of Biotechnology, 2017, 251: 145-150".

The *Aureobasidium pullulans* original P30 strain provided by the present invention has been preserved in China General Microbiological Culture Collection Center (CGMCC) according to the Budapest Treaty with the preservation number of CGMCC No. 13988 on Apr. 6, 2017 in Institute of Microbiology, Chinese Academy of Sciences, 3, NO. 1 Beichen West Road, Chaoyang District, Beijing, China.

The functions of the *Aureobasidium pullulans* P30 strain are similar to those of general *Aureobasidium pullulans* strains except for high heavy oil productivity.

The present invention has the following advantages:

Liamocins (Liamocin oils) have great potential for medical applications due to the anti-cancer properties thereof. According to the present invention, by knocking out (substituting) a pullulan synthetase PUL gene while overexpressing the ACL gene, the obtained *Aureobasidium pullulans* recombinant strain can significantly increase the yield of heavy oil. After 7-day fermentation with xylose as the carbon source, the yield of the heavy oil of the recombinant strain reaches 19.4372 g/L, while the yield of the heavy oil of a parent strain is 10.0325 g/L, i.e. the recombinant strain improves the yield by 93.74% compared with the parent strain.

Figure 3:
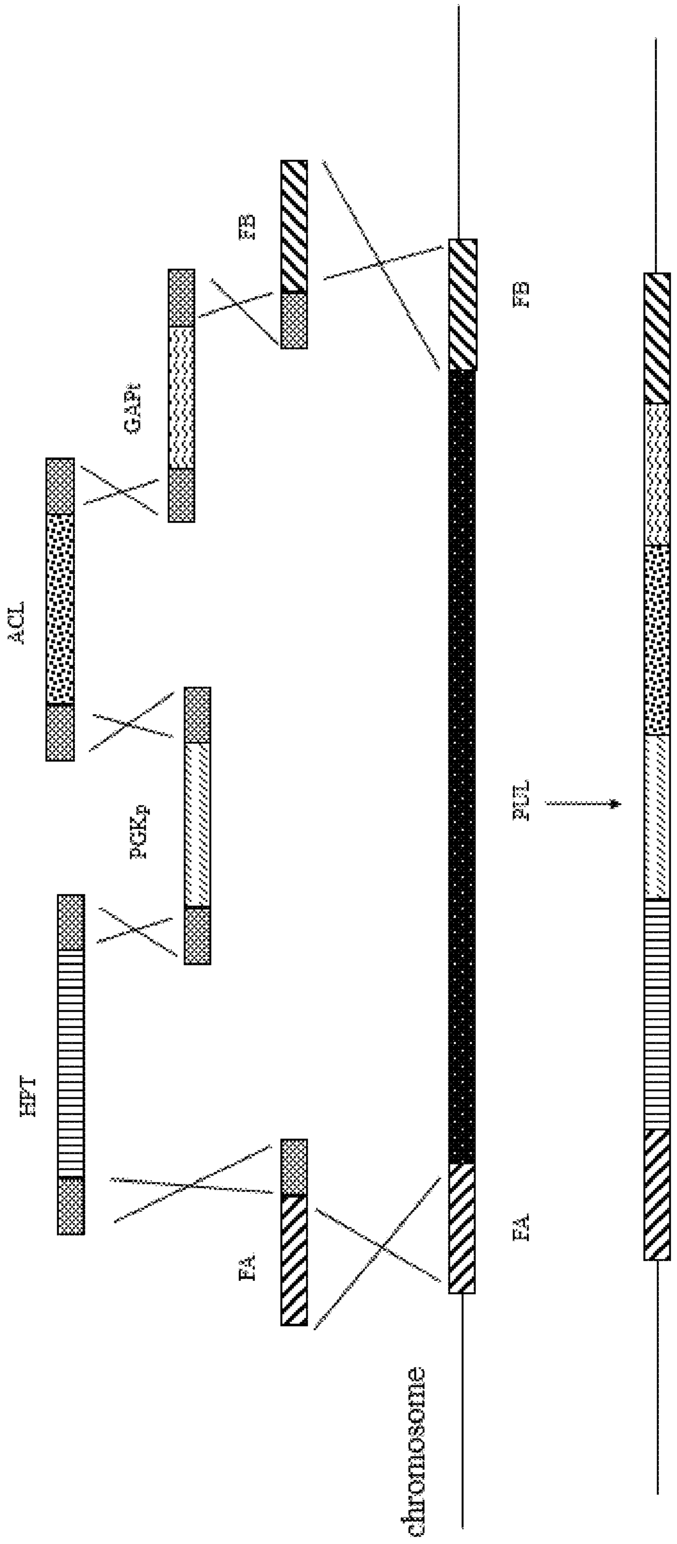
Figure 4:
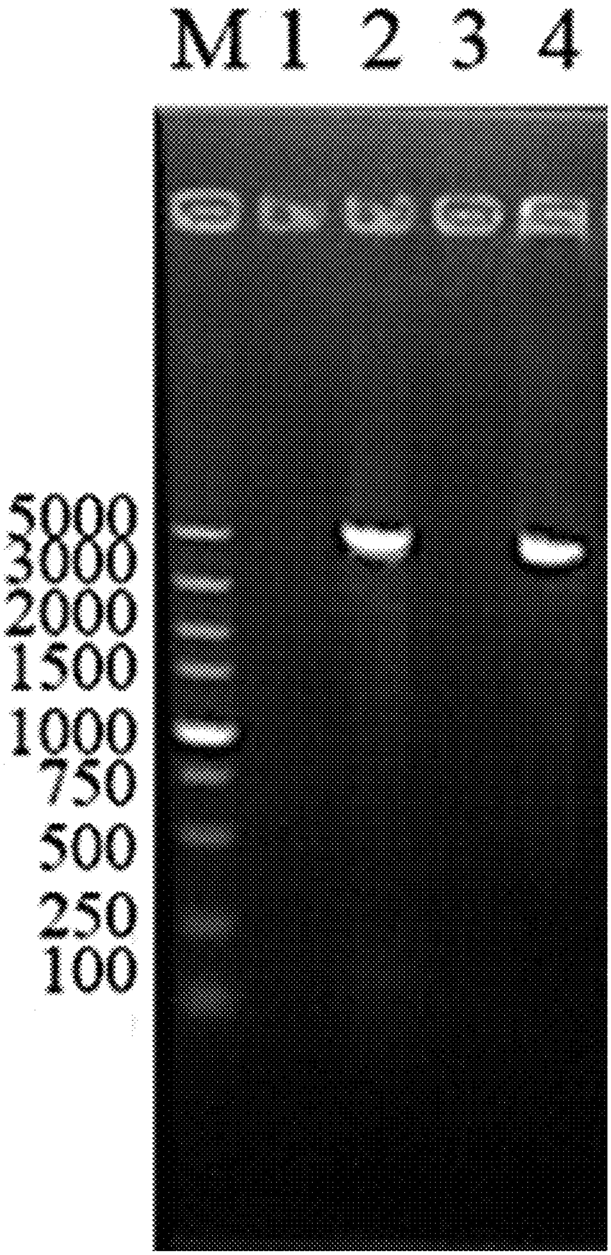
Figure 5A:
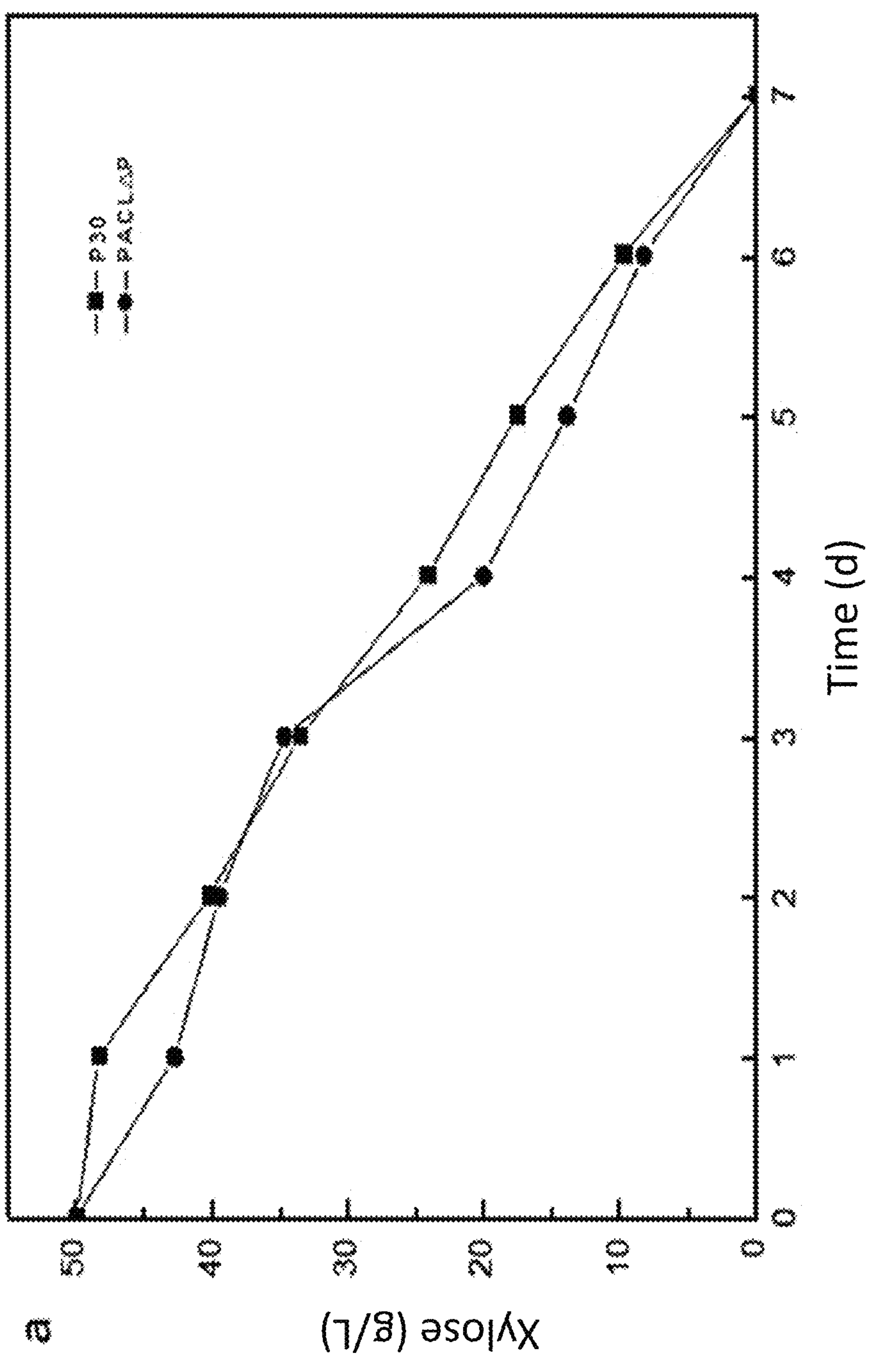
Figure 5B:
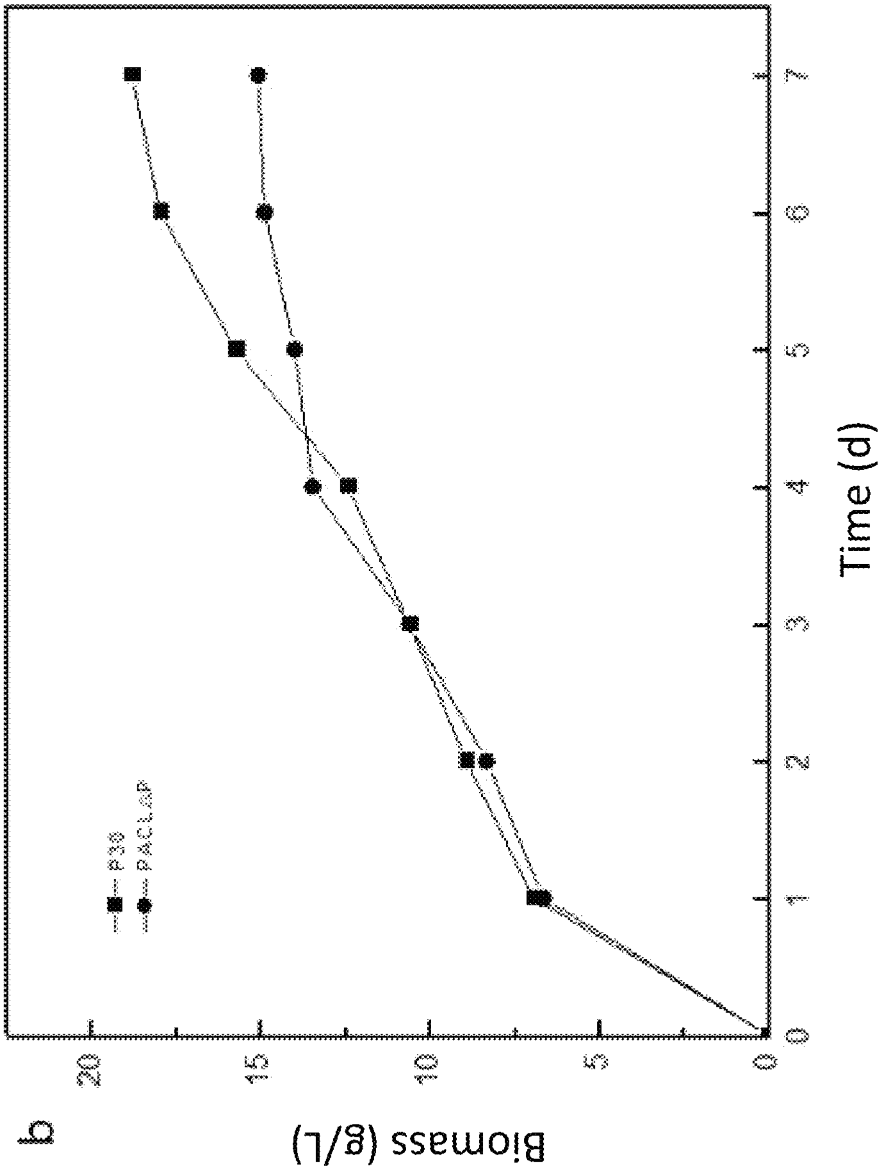

wherein the lane M: 5000 bp DNA maker; lane 1: fragment obtained by PCR using PUC19 as template, and PUC-U and PUC-D as primers; lane 2: fragment obtained by PCR using pUC-HPT as template, and PUC-U and PUC-D as primers;

FIG. 3 is a diagram showing the process of homologous recombination of the *Aureobasidium pullulans* recombinant strain overexpressing the ACL gene;

FIG. 4 shows verification result of the recombinant strains of *Aureobasidium pullulans* overexpressing the ACL gene:

wherein the lane M: 5000 bp DNA maker; lane 1: fragment obtained by PCR using the original strain as template, and PUL-U and PGK-D as primers; lane 2: fragment obtained by PCR using the recombinant strain as template, and PUL-U and PGK-D as primers; lane 3: fragment obtained by PCR using the original strain as template, and PGK-U and PUL-D as primers (cross validation fragment); lane 4: fragment obtained by PCR using the recombinant strain as template, and PGK-U and PUL-D as primers;

FIGS. 5A-5B shows a comparison of xylose utilization and biomass between the recombinant strain (PACLΔP) and the original strain (P30), wherein FIG. 5A shows xylose consumption curves and FIG. 5B shows biomass change curves.

DETAILED DESCRIPTION OF THE EMBODIMENTS

The present invention is described below with reference to specific embodiments. Unless otherwise specified, the technical means used in the present invention are all well known to those skilled in the art. In addition, the embodiments should be considered illustrative and not restrictive to the scope of the present invention. The essence and scope of the present invention is defined solely by the claims. For those skilled in the art, various changes or modifications in the components and amounts of the materials used in the embodiments should be made without departing from the spirit and scope of the invention and shall fall in the scope of protection of the present invention.

Embodiment 1: Construction of the *Aureobasidium pullulans* Recombinant Strain Capable of Improving Heavy Oil Production Capacity The original strain used in the embodiment was *Aureobasidium pullulans* P30, the *E. coli* DH5a was purchased from Takara, the YPD culture medium was a general complete culture medium, and the solid culture medium contained 2% agar powder.

The following primers were designed based on the *Aureobasidium pullulans* genome data and the integration plasmid sequence. KpnI restriction sites were underlined.

TABLE 2

PCR amplification system used in the Embodiment 1.

|  | 20 µL system (µL) | 50 µL system (µL) |
| --- | --- | --- |
| 10 × PCR Buffer | 2.0 | 5.0 |
| dNTP (2.5 mmol/L) | 1.5 | 4.0 |
| Upstream primer (10 µmol/L) | 1.0 | 1.0 |
| Downstream primer (10 µmol/L) | 1.0 | 1.0 |
| Template | 1.0 | 1.5 |
| rTaq enzyme | 0.5 | 1.0 |
| ddH$_2$O | Add to 20 | Add to 50 |

TABLE 3

PCR amplification system used in the Embodiment 1.

|  | 50 µL system (µL) |
| --- | --- |
| 5 × primeSTAR Buffer (Mg$^{2-}$ Plus) | 10 |
| dNTP Mixture | 4 |
| Upstream primer | 1 |

TABLE 1

The primers used in the Embodiment 1.

| SEQ ID NO | Primer | 5'→3' |
| --- | --- | --- |
| 7 | PTEFP-U | CTAGAGGATCCCCG**GGTACC**GTCAAGACAGCAAGAACGGG |
| 8 | TEFpH-D | CGGTGAGTTCAGGCTTTTTCATGTTGACGGTTGTGTATGGAA |
| 9 | TEFpH-U | TTCCATACACAACCGTCAACATGAAAAAGCCTGAACTCACCG |
| 10 | HTEFt-D | AGACAAAAGTGTCAAATCGTCTATTCCTTTGCCCTCGGAC |
| 11 | HTEFt-U | GTCCGAGGGCAAAGGAATAGACGATTTGACACTTTTGTC |
| 12 | TEFtP-D | GTGAATTCGAGCTC**GGTACC**TCTTCCCTTTCACTAGGTCG |
| 13 | PUC-U | TGATTACGCCAAGCTTGCATGC |
| 14 | PUC-D | GTAAAACGACGGCCAGTGAATTC |
| 15 | FA-U | TCGGCATCTATTTTGAGATGCTG |
| 16 | FA-D | GTGTTCCCGTTCTTGCTGTCTTGACGGTTGTTAGGAGATAGAATGGTTG |
| 17 | H-U | GCAACCATTCTATCTCCTAACAACCGTCAAGACAGCAAGAACGGGAACAC |
| 18 | H-D | GAGAGGTTACCTAAGTGAGGCAATGTCTTCCCTTTCACTAGGTCG |
| 19 | PKG-U | CTGTCCGACCTAGTGAAAGGGAAGACATTGCCTCACTTAGGTAACC |
| 20 | PKG-D | GAGGATCGACTTTGCGGACATTGTGACTGAATCGAGTGTGTC |
| 21 | ACL-U | GTCTGACACACTCGATTCAGTCACAATGTCCGCAAAGTCGATCCTC |
| 22 | ACL-D | GCTTGGTCATACGCACATCAGAGATATGCACCGAACTCCTTGATGTC |
| 23 | GAP-U | GACATCAAGGAGTTCGGTGCATATCTCTGATGTGCGTATGACCAAGC |
| 24 | GAP-D | GTTGGTAGTAGGGATCGAAGAGGGTCTAAGGTCATGGTTTCTCTG |
| 25 | FB-U | CTGCCCAGAGAAACCATGACCTTAGACCCTCTTCGATCCCTACTACC |
| 26 | FB-D | TAGTAAGGCACAGTCAAAGC |
| 27 | PUL-U | AGAAGGCTGTGTAGCTGTACGACC |
| 28 | PUL-D | TTAGTAAGGCACAGTCAAAGCAG |

TABLE 3-continued

| PCR amplification system used in the Embodiment 1. | |
| --- | --- |
| | 50 μL system (μL) |
| Downstream primer | 1 |
| Template DNA | 1 |
| PrimeSTAR HS | 0.5 |
| $ddH_2O$ | 32.5 |

(1) Construction of Recombinant Plasmid pUC-HPT

Figure 1:
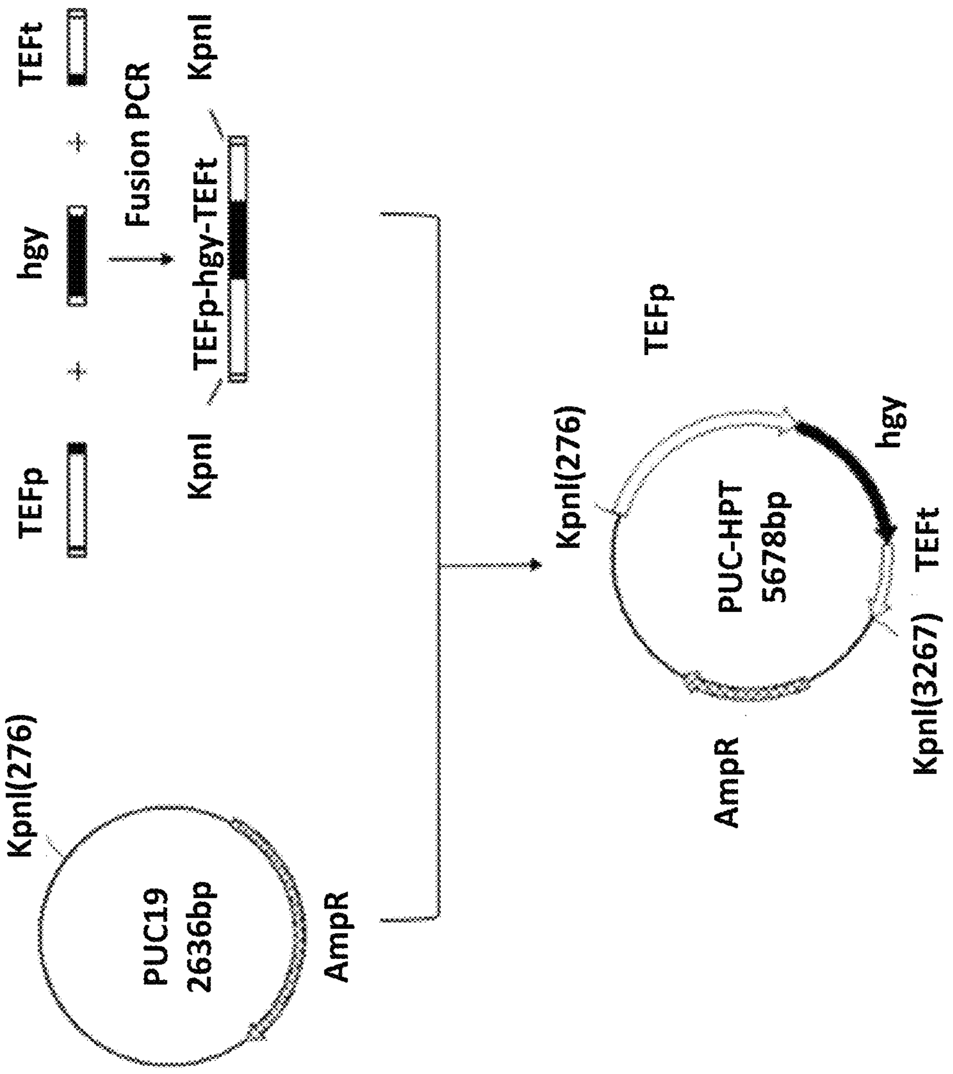
FIG. 1 shows a flow diagram of construction of the pUC-HPT plasmid.
Figure 2:
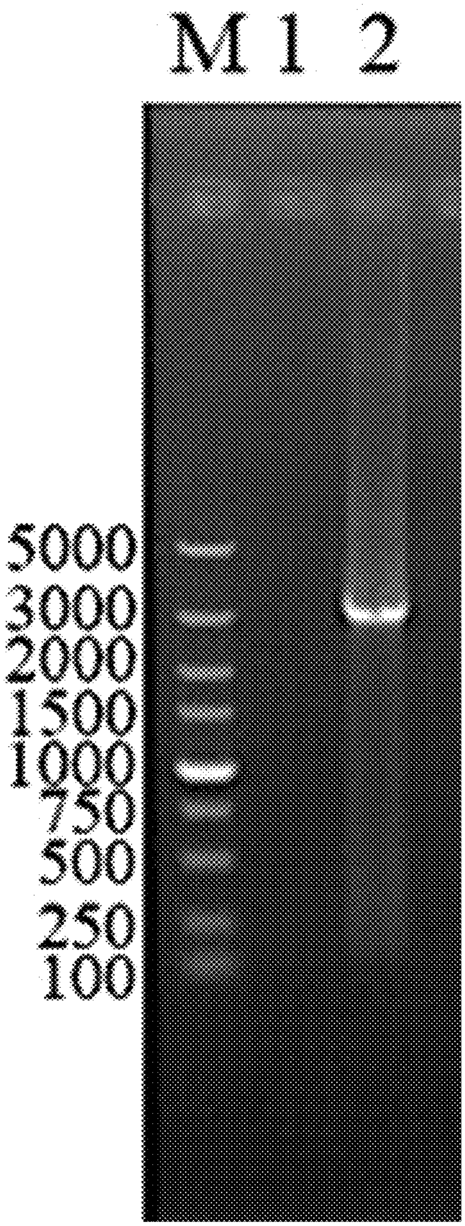
FIG. 2 is an electrophoretogram showing the verification of construction of the pUC-HPT plasmid.

The construction process of the recombinant pUC-HPT plasmid is shown in FIG. 1. Firstly, the genome of the *Aureobasidium pullulans* P30 strain was taken as a template, the primers PTEFP-U and TEFpH-D were applied to amplification to obtain a TEF promoter fragment of 1500 bp (SEQ ID NO: 3), the primers HTEFt-U and TEFtP-D were applied to amplification to obtain a TEF terminator of 500 bp (SEQ ID NO: 4). Yep-HPT plasmid was taken as a template and TEFpH-U and HTEFt-D as primers to perform amplification to obtain an hyg fragment of 1026 bp in length; the TEF promoter, the hygromycin (hyg) resistance gene and the TEF terminator were connected together through fusion PCR to obtain TEFp-hyg-TEFt (KpnI restriction sites were added during design of the upstream primers of the promoter and the downstream primers of the terminator to obtain the TEFp-hyg-TEFt fragment with the KpnI restriction sites at both ends), and the TEFp-hyg-TEFt fragment was subjected to KpnI enzyme digestion and then connected to a pUC19 plasmid also subjected to KpnI enzyme digestion to obtain a pUC-HPT plasmid. The electrophoretogram of verification of construction of the pUC-HPT plasmid is shown in FIG. 2.

(2) Construction of the *Aureobasidium pullulans* Recombinant Strain

The genome of the *Aureobasidium pullulans* P30 strain was taken as a template to carry out PCR amplification to obtain the upper and lower homologous arms FA and FB of the pullulan synthetase PUL gene (nucleotides 85-511 and nucleotides 571-989 of SEQ ID NO: 2, respectively), a PGK promoter (SEQ ID NO: 5), a GAP terminator (SEQ ID NO: 6) and an ACL gene (SEQ ID NO: 1) which are respectively 430 bp, 430 bp, 1454 bp, 620 bp and 1462 bp in length. Meanwhile, the pUC-HPT plasmid was taken as a template to perform PCR to obtain the hygromycin resistance gene TEFp-hyg-TEFt. Electrotransformation was performed to sequentially connect and integrate the PCR amplification products of the upper homologous arm FA, the hyg resistance gene fragment, the PGK promoter, the ACL gene, the GAP terminator and the downstream homologous arm FB into the sites of the pullulan synthetase PUL gene of the original strain of the *Aureobasidium pullulans* P30 strain. Plates containing 150 mg/L hygromycin B were used for screening to obtain a homologous recombinant strain. The process of homologous recombination of the *Aureobasidium pullulans* recombinant strain overexpressing the ACL gene is shown in FIG. 3, and the verification of the recombinant strain is shown in FIG. 4.

(3) Verification of the *Aureobasidium pullulans* Recombinant Strain:

According to the gene sequences at both ends of the *Aureobasidium pullulans* recombination sites and the inserted homologous recombination sequences, two groups of upstream and downstream primers, namely PUL-U, PGK-D, PGK-U and PUL-D, were designed respectively. The genome of a transformant with better growth was taken as a template to perform PCR amplification to verify the recombinant; the PCR products were subjected to 0.8% agarose gel electrophoresis, respectively; an 4900 bp band was obtained by upstream verification, and a 3972 bp band was obtained by downstream verification, which show that an ACL gene expression cassette was successfully integrated into the *Aureobasidium pullulans* P30 strain.

Embodiment 2: Fermentation Experiment of the Recombinant Strain by Taking Xylose as a Carbon Source The recombinant strain seed was inoculated into a seed culture medium and subjected to shaking culture at 28° C. and 240 r/min for 24 hours to obtain a seed solution; the seed solution was inoculated at an inoculum size of 6% into a fermentation culture medium and subjected to shake flask fermentation at 28° C. and 240 r/min for 7 days.

The seed culture medium was composed of 20 g/L of xylose, 1.0 g/L of yeast extract powder 4.0 g/L of $K_2HPO_4$, 0.8 g/L of $(NH_4)_2SO_4$, 0.2 g/L of $MgSO_4$, 4.0 g/L of NaCl and water as balance; the pH was 6.0, and sterilization was performed at 121° C. for 20 min.

The fermentation medium was composed of 50 g/L of xylose, 2.0 g/L of yeast extract powder, 0.8 g/L of $KNO_3$, 2.0 g/L of NaCl, 5.0 g/L of $K_2HPO_4$, 0.3 g/L of $MgSO_4$ and water as balance; the pH was 5.0, and sterilization was performed at 121° C. for 20 min.

The fermentation experiment was performed on the original *Aureobasidium pullulans* P30 strain and the selected strain PACLΔP by taking the xylose as the carbon source under the fermentation conditions above. Sampling was performed every 24 hours during fermentation to determine residual sugar and biomass, and the results are shown in FIG. 5. The content of pullulan and heavy oil after the fermentation were determined, and the results are shown in TABLE 4.

As shown FIG. 5A, the xylose consumption curve of the recombinant strain is basically consistent with that of the original P30 strain, and the fermentation liquid had no xylose residue 7d (d=days) after fermentation, which indicates that the xylose utilization capability of the recombinant strain is not affected. The overall growth trend of the recombinant strain in FIG. 5B is relatively consistent to that of the original P30 strain, the growth conditions and other growth functions of the recombinant strain are overall not greatly affected, and the biomass of the recombinant strain is 19.83% lower than that of the original strain after fermentation.

TABLE 4

Yields of pullulan and heavy oil produced by fermentation with the xylose as the carbon source.

| Strain | Pullulan (g/L) | Heavy Oil (g/L) |
| --- | --- | --- |
| P30 | 8.5417 | 10.0325 |
| PACLΔP | 7.5250 | 19.4372 |

Note:
data shown are the average of the results of three parallel experiments.

TABLE 4 shows that: in the fermentation experiment with the xylose as the carbon source, the yields of pullulan and heavy oil produced by the *Aureobasidium pullulans* strain obtained in the present invention change. The yield of the pullulan of the original P30 strain was 8.5417 g/L, while the yield of the pullulan of the recombinant strain obtained by the present invention was 7.5250 g/L, which is 11.9% lower compared with the original strain. The result indicates that the recombinant strain reduces the production of the byproduct of the pullulan to some extent. The yield of the heavy oil of the recombinant strain reached 19.4372 g/L, while the yield of the heavy oil of a parent strain was 10.0325 g/L, namely the recombinant strain improves the yield by 93.74% compared with the parent strain. The result indicates that the heavy oil productivity of the strain obtained in the invention is greatly improved, and thereby a theoretical basis is provided for selecting high-yield heavy oil producing *Aureobasidium pullulans* strains.

What is claimed is:

1. An *Aureobasidium pullulans* recombinant strain, wherein the *Aureobasidium pullulans* recombinant strain improves a yield of heavy oil, and the *Aureobasidium pullulans* recombinant strain is achieved by using an *Aureobasidium pullulans* P30 strain as an original strain, using an ATP-citrate lyase (ACL) gene as a substitute for a pullulan synthetase (PUL) gene, and overexpressing the ACL gene with a promoter, wherein the nucleotide sequence of the ACL gene comprises SEQ ID NO: 1, the nucleotide sequence of the PUL gene comprises SEQ ID NO: 2, and the preservation number of the *Aureobasidium pullulans* P30 strain is CGMCC No. 13988.

2. The *Aureobasidium pullulans* recombinant strain according to claim 1, wherein the promoter is a PGK promoter, and the nucleotide sequence of the PGK promoter is as SEQ ID NO: 5.

3. A method of making the *Aureobasidium pullulans* recombinant strain according to claim 1, comprising the following steps:

obtaining an *Aureobasidium pullulans* P30 strain as the original parent strain;

sequentially connecting and integrating an upstream homologous arm FA of the PUL gene of the *Aureobasidium pullulans* P30, a hygromycin resistance gene (hyg) fragment, a PGK promoter, the ACL gene of the *Aureobasidium pullulans* P30 strain, a GAP terminator and a downstream homologous arm FB of the PUL gene of the *Aureobasidium pullulans* P30 strain into a PUL gene integration site of the *Aureobasidium pullulans* P30 strain; and performing homologous recombination to obtain the *Aureobasidium pullulans* recombinant strain of claim 1, wherein the nucleotide sequence of the PGK promoter is SEQ ID NO: 5, and the nucleotide sequence of the GAP terminator is SEQ ID NO: 6.

4. The method of making the *Aureobasidium pullulans* recombinant strain according to claim 3, specifically comprising the following steps:

carrying out a first PCR amplification with a genome of the *Aureobasidium pullulans* P30 strain as a template to obtain PCR amplification products of the upstream homologous arm FA and the downstream homologous arm FB of the PUL gene, the PGK promoter, the GAP terminator and the ACL gene;

carrying out a second PCR amplification on a plasmid carrying a hyg resistance gene to obtain a PCR amplification product of the hyg resistance gene fragment; and performing an electrotransformation to sequentially connect and integrate the PCR amplification products of the upstream homologous arm FA of the PUL gene, the hyg resistance gene fragment, the PGK promoter, the ACL gene, the GAP terminator and the downstream homologous arm FB of the PUL gene into the PUL gene integration site of the *Aureobasidium pullulans* P30 strain, and performing the homologous recombination to obtain the *Aureobasidium pullulans* recombinant strain of claim 1 overexpressing the ACL gene with the PGK promoter.

5. A method to produce a heavy oil, comprising culturing the *Aureobasidium pullulans* recombinant strain according to claim 1 under fermentation conditions, wherein the fermentation results in production of heavy oil.

6. The method according to claim 5, comprising the following steps:

selecting and inoculating a strain seed of the *Aureobasidium pullulans* recombinant strain according to claim 1 into a seed culture medium, and performing shake culture at 28-30° C. and 200-240 r/min for 20-24 h to obtain a seed solution;

inoculating the seed solution at an inoculum size of 6%-8% into a fermentation culture medium, and performing a shake flask fermentation at 28-30° C. and 200-240 r/min for 5-7 days;

wherein the seed culture medium comprises 20 g/L of xylose, 1.0 g/L of yeast extract powder, 4.0 g/L of $K_2HPO_4$, 0.8 g/L of $(NH_4)_2SO_4$, 0.2 g/L of $MgSO_4$, 4.0 g/L of NaCl and water as balance, with a pH of 5.5-6.5, and the seed culture medium is subjected to sterilization at 121° C. for 20 min; and the fermentation culture medium comprises 50 g/L of xylose, 1.4-2.0 g/L of yeast extract powder, 0.8 g/L of KNOB, 2.0 g/L of NaCl, 5.0 g/L of $K_2HPO_4$, 0.3 g/L of $MgSO_4$ and water as balance, with a pH of 4.5-5.5, and the fermentation culture medium is subjected to sterilization at 121° C. for 20 min.

* * * * *